(12) United States Patent
Krainer et al.

(10) Patent No.: US 7,767,740 B2
(45) Date of Patent: Aug. 3, 2010

(54) ALKYLTIN SULFANYL MERCAPTOCARBOXYLATES HAVING TERMINAL THIOL GROUPS

(75) Inventors: Edward Krainer, Lynbrook, NY (US); Peter Frenkel, Danbury, CT (US); Mukund Shah, Hazlet, NJ (US); Perry Reed, Matanan, NJ (US); David J. Sikora, Middlebury, CT (US)

(73) Assignee: Galata Chemicals, LLC, New York, NY (US)

( * ) Notice: Subject to any disclaimer, the term of this patent is extended or adjusted under 35 U.S.C. 154(b) by 408 days.

(21) Appl. No.: 11/124,464

(22) Filed: May 5, 2005

(65) Prior Publication Data

US 2006/0252859 A1   Nov. 9, 2006

(51) Int. Cl.
*C08K 5/00* (2006.01)

(52) U.S. Cl. ...................................................... 524/180

(58) Field of Classification Search ................... 524/180
See application file for complete search history.

(56) References Cited

U.S. PATENT DOCUMENTS

| | | | |
|---|---|---|---|
| 2,752,325 A | 6/1956 | Leistner et al. | 260/45.75 |
| 4,111,903 A | 9/1978 | Hoch et al. | 260/45.75 |
| 4,546,136 A | 10/1985 | Cooray | 524/180 |
| 6,180,832 B1 | 1/2001 | Frenkel et al. | 568/561 |
| 6,225,510 B1 | 5/2001 | Frenkel et al. | 568/558 |
| 6,379,711 B1 | 4/2002 | Frenkel et al. | 424/616 |
| 6,756,431 B2 | 6/2004 | Shah et al. | 524/100 |
| 6,835,328 B2 | 12/2004 | Fakinlede et al. | 252/400.52 |

FOREIGN PATENT DOCUMENTS

| | | |
|---|---|---|
| GB | 748228 | 4/1956 |
| GB | 866484 | 4/1961 |

*Primary Examiner*—Edward J Cain
(74) *Attorney, Agent, or Firm*—Dilworth IP, LLC

(57) ABSTRACT

An alkyltin compound of specified formula which has utility as an excellent stabilizer for a halogen-containing resin. The alkyltin compound has from 1-3 terminal thiol groups.

15 Claims, 1 Drawing Sheet

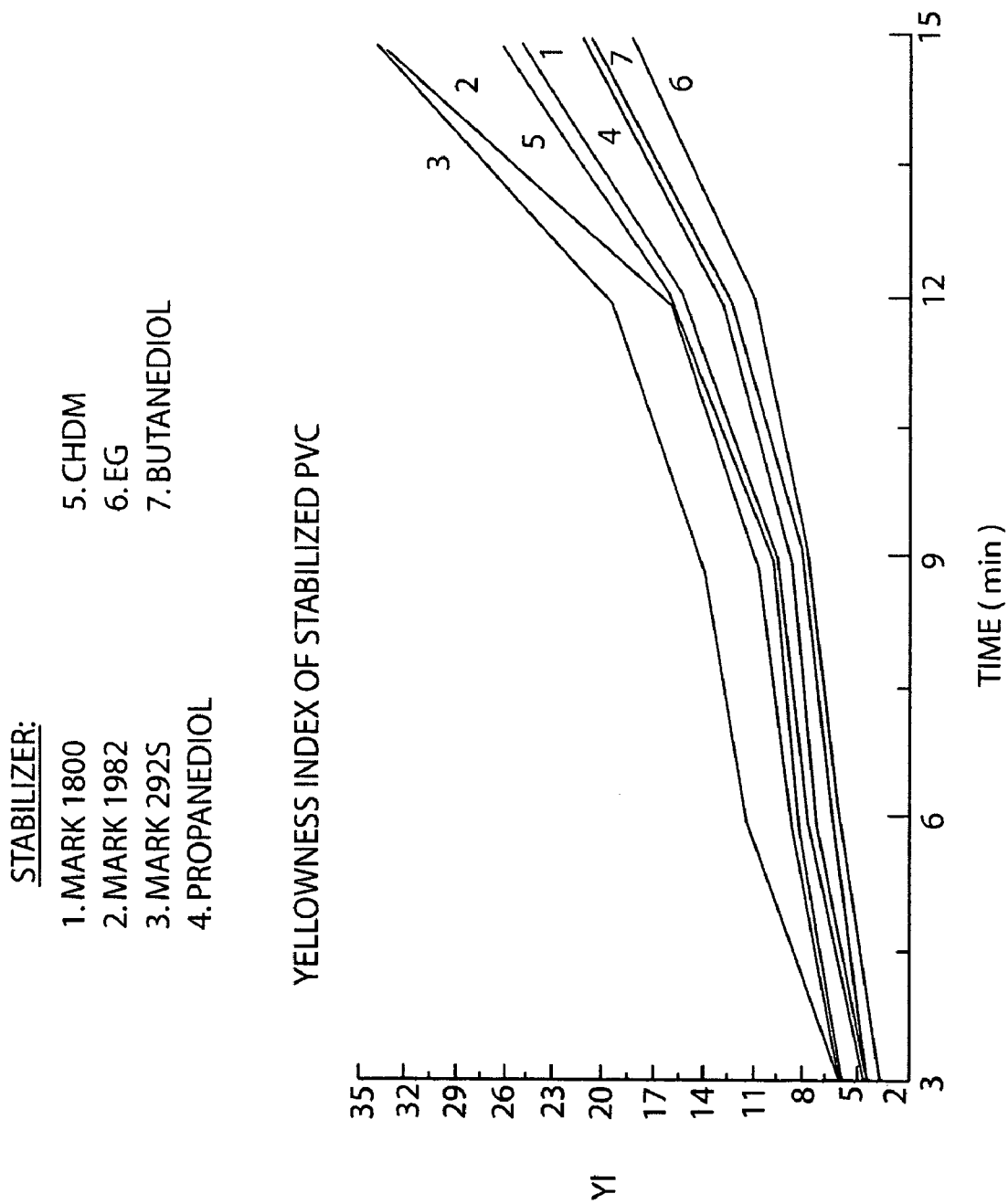

ALKYLTIN SULFANYL MERCAPTOCARBOXYLATES HAVING TERMINAL THIOL GROUPS

BACKGROUND OF THE INVENTION

1. Field of the Invention

This invention relates to alkyltin thermal stabilizers for halogen-containing resin compositions. More particularly, the present invention relates to alkyltin sulfanyl mercaptocarboxylates having from one to three terminal thiol groups and which are suitable for thermal stabilization of polyvinyl compositions.

2. Description of the Prior Art

British Patent Specification No. 866,484 generically discloses alkyltin sulfanyl derivatives having terminal thiol groups, which are said to stabilize vinyl resins against the degradative effects of both heat and light. However, no experimental data is provided to quantify these claims for any of these compounds.

Non-thiol terminated alkyltin stabilizers are also known. For example, dimethyltin bis S,S(2-ethylhexanol thioglycolate) and di-n-butyl bis S,S(2-ethylhexanol thiolglycolate) are both commercially available. One of the most effective thermal stabilizers is a blend of dimethyltin bis S,S (2-ethylhexanol thioglycolate) and methyltin tris S,S,S(2-ethylhexanol thioglycolate). These compounds are also commercially available.

SUMMARY OF THE INVENTION

In one aspect, the present invention relates to an alkyltin compound having the formula:

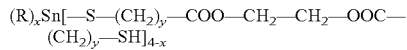

$$(R)_x Sn[-S-(CH_2)_y-COO-CH_2-CH_2-OOC-(CH_2)_y-SH]_{4-x}$$

wherein:

R is a $C_{1-3}$ alkyl group;
x is equal to 1 or 2;
y is equal to 1 or 2.

These organotin compounds may be generally described as condensation products of organotin derivatives (such as oxides and chlorides) and dimercaptoacid esters of ethylene glycol.

In a second aspect, the present invention relates to a composition which includes a halogen-containing resin and an alkyltin compound as described above in an amount effective to stabilize the resin against elevated temperatures, UV light, oxidation and high shear forces.

BRIEF DESCRIPTION OF THE DRAWING

FIG. 1 is a graph of yellowness index of sample chips taken at various times during a heat stability test. The graph illustrates the improved color stability of a rigid PVC formulation containing the new tin stabilizer in comparison to control formulations containing other organotin compounds present at the same tin level.

DETAILED DESCRIPTION OF THE PREFERRED EMBODIMENTS

The alkyltin compounds of Formula 1 preferably have methyl groups for R.

Alkyltin compounds which come within Formula I and which are particularly preferred include dimethyltin bis(1,2-ethane dithioglycolate), monomethyltin tris(1,2-ethanedithioglycolate), dimethyltin bis(1,2-ethane dimercaptopropionate), monomethytin tris(1,2-ethanedimercaptopropionate) and mixtures thereof.

Those of ordinary skill in the art will recognize the alkyltin compounds of the present invention may be prepared via several synthetic routes. In a preferred embodiment, these alkyltin compounds may be conveniently synthesized using a two-reaction procedure which employs readily available reactants. First, a dithiol ester is prepared by esterification of ethylene glycol with a thioacid in a molar ratio of 1:2 in the presence of a suitable catalyst. It is preferred to use a slight excess (3-5%) of thioglycolic acid. Suitable thioacids include mercaptoacetic acid and mercaptopropionic acid. Appropriate catalysts include but are not limited to p-toluene sulfonic acid and methane sulfonic acid.

The esterification reaction may be performed with or without a solvent at an appropriate temperature, for example, 130-150° C. Water formed during the reaction is removed by conventional methods.

The resulting dithiol ester may be neutralized with an appropriate base such as sodium bicarbonate or potassium carbonate, purified by filtering salt residues and stripped under vacuum to remove moisture, preferably at an elevated temperature such as, for example, 60-80° C.

In the second stage of the synthesis, the dithiol ester is reacted with an appropriate tin-containing reactant, for example an alkyltin chloride or alkyltin oxide, at the following molar ratios: for dialkyltin derivatives S:Sn>1.5 and for monoalkyltin derivatives S:Sn>1.0. The resulting alkyltin compound thus contains both Sn—S bonds and free, terminal thiol groups.

The alkyltin compounds of the present invention impart superior thermal stability to halogen-containing resins. Such resins include polyvinyl chloride (PVC), polyvinyl bromide, polyvinylidene chloride, copolymers of vinyl chloride and vinyl acetate, copolymers of vinyl chloride and vinylidene chloride, copolymers of vinyl chloride and acrylonitrile, copolymers of vinyl chloride and maleic or fumaric esters and copolymers of vinyl chloride and styrene.

An effective amount of the alkyltin compound is an amount which makes the halogen-containing resin more resistant to discoloration than the resin per se. Generally, an effective amount will range from 0.5 to 1.50 parts stabilizer per hundred parts resin, and will depend on the specific resin and alkyltin compound, as well as the degree of thermal stabilization desired. A preferred amount of alkyltin compound is from 0.8 to 1.2 parts stabilizer per hundred parts resin.

The alkyltin compound may be added to the halogen-containing resin using techniques and apparatus well known to those of ordinary skill in this art. Generally, the resin may be mixed with the stabilizer in a high speed mixer for 30-90 seconds to thoroughly disperse the alkyltin compound throughout the resin.

The halogen-containing resin may also contain known additives as long as their presence does not materially degrade the thermal stability imparted by the alkyltin compounds of the present invention. Such additives include, without limitation, lubricants, fillers, pigments, flame retardants, UV absorbers, impact modifiers and processing aids. These additives may be added to the resin using techniques and apparatus well known to those of ordinary skill in this art.

Suitable lubricants include calcium stearate, montan wax, fatty acid esters, polyethylene waxes, chlorinated hydrocarbons, glycerol esters and combinations thereof.

Suitable fillers include titanium oxide, calcium carbonate, kaolin, glass beads, glass fibers, talc, wood flour and mixtures thereof.

Suitable pigments include azo pigments, phthalocyanine pigments, quinacridone pigments, perylene pigments, diketopyrrolopyrrole pigments and anthraquinone pigments.

Suitable flame retardants include antimony oxide, molybdates, borates and hydroxystannates.

EXAMPLES

The following Examples illustrate the practice and advantages of specific embodiments of the invention. The Examples are not intended to limit the invention in any manner whatsoever.

Example 1

Synthesis of dimethyltin bis(1,2-ethane dithioglycolate)

62 g ethylene glycol was reacted with 191.2 g thioglycolic acid (TGA) in the presence of 1 g p-toluenesulfonic acid (p-TSA) at 110-150° C. Over a period of 5 hours, 34 g water was collected (theory water 36 g). The batch was neutralized with 5 g $K_2CO_3$ and filtered to yield 214 g of clear product. The acid value after neutralization was 0.051 meq/g. Mercaptan value by iodine titration was 28.74%. Gas chromatographic analysis showed no ethylene glycol and 12.6% mono-thioglycolate and 80% di-thioglycolate.

100.7 g of the di-thioglycolate (1,2-ethane dithioglycolate) was reacted with 50.13 g dimethyltin dichloride dissolved in 150 ml water. The reaction mix was neutralized to pH 6.5 using ammonium hydroxide solution. The crude product was separated from the aqueous phase and stripped at 80° C. and 2-5 mm Hg for 2 hours using a Buchi Rotovapor R-134 evaporator. The product was filtered hot to remove traces of residual salts to yield 104 g of the clear product. Analysis: sulfur found 22.34%, calculated 22.62; tin found 20.75%, calculated 20.85%.

Corresponding dimethyltin sulfanyl mercaptocarboxylates prepared from 1,3-propylene glycol, 1,4-butanediol and 1,4-cyclohexanedimethanol, respectively, and which were prepared in analogous manner, were used as controls.

Example 2

Evaluation of Color Stability

Rigid PVC formulations were prepared using the stabilizer of Example 1, the control stabilizers derived from diols of higher (than ethylene glycol) molecular weight and commercially available alkyltin stabilizers, such as dimethyltin-bis(2-ethylhexylthioglycolate) (Mark 1982), dibutyltin-bis(2-ethylhexylthioglycolate) (Mark 292S), and a blend of monomethyltin-tris(2-ethylhexylthioglycolate) with dimethyltin-bis(2-ethylhexylthioglycolate) (Mark 1900). The tin content in the formulations was the same for all samples. Each PVC compound test sample was placed into a Brabender mixer operated at 190° C. and 65 RPM. Sample chips were taken every three minutes. Fusion time was about the same for all samples.

Color stability was determined from sample chips using a Hunter Lab calorimeter measuring Yellowness Index (YI) (lower YI signifies lesser discoloration as a result of thermal decomposition and, therefore, superior thermal stabilization). See Table 1 and FIG. 1.

TABLE 1

Yellowness Index of PVC and analytical data on heat stabilizers

| Time, min. | Mark 1900 | Mark 1982 | Mark 292S | 1,3-propanediol derivative | 1,4-CHDM derivative | EG derivative | 1,4-BG derivative |
|---|---|---|---|---|---|---|---|
| 3 | 4.18 | 4.35 | 5.91 | 4.49 | 6.00 | 3.59 | 5.72 |
| 6 | 6.28 | 7.84 | 11.46 | 7.29 | 8.77 | 5.99 | 8.31 |
| 9 | 8.09 | 9.96 | 14.29 | 8.93 | 10.97 | 7.93 | 9.76 |
| 12 | 12.55 | 16.13 | 19.78 | 13.01 | 15.84 | 11.21 | 15.29 |
| 15 | 20.69 | 33.30 | 34.03 | 21.37 | 26.21 | 18.41 | 25.12 |
| Stabilizer Tin content, % | 19.40 | 19.67 | 18.08 | 18.65 | 15.62 | 20.85 | 19.00 |
| Stabilizer added, phr | 1.20 | 1.18 | 1.29 | 1.25 | 1.49 | 1.12 | 1.23 |
| Tin amount added, phr | 0.23 | 0.23 | 0.23 | 0.23 | 0.23 | 0.23 | 0.23 |

Note:
"1,3-propanediol derivative" is dimethyl bis (1,3-propane dithioglycolate);
"1,4-CHDM derivative" is dimethyltin bis(1,4-cyclohexane dithioglycolate);
"EG derivative" is dimethyltin bis (1,2-ethane dithioglycolate); and
"1,4-BG derivative" is dimethyltin bis(1,4-butane dithioglycolate).
"Initial color hold" refers to yellowing resistance during the first 3 to 10 minutes of the Brabender color stability test. Monoalkyltin stabilizers are known to provide an excellent initial color-hold.
"Long term heat stability" refers to yellowing resistance at sample times greater than 10 minutes in the Brabender color stability test. Dialkyltin stabilizers are known to provide superior long-term heat stability.

Blends of the monoalkyltin and dialkyltin moieties provide the most efficient balance of both initial color-hold and long-term heat stability. One such blend is a mixture of monomethyltin tris-(2-ethylhexylthioglycolate) and dimethyltin bis-(2-thioglycolate), which is commercially available from Crompton Corporation under name Mark 1900.

Added at the same tin content, the dimethyltin bis(1,2-ethanedithioglycolate) stabilizer of the present invention achieved an initial color stability similar to that of the Mark 1900 blend, as measured by yellowness index (from 3 to about 10 minutes in the Brabender test; see Table 1 and FIG. 1). In other words, the dimethyltin bis(1,2-ethanedithioglycolate) stabilizer was unexpectedly effective in initial color stabilization despite the absence of a monoalkyltin moiety in its composition.

The dimethyltin bis(1,2-ethanedithioglycolate) stabilizer also exhibited superior long-term heat stability in comparison to the Mark 1900 blend, as demonstrated by the yellowness index curves from 10-15 minutes during the Brabender color stability test.

Although the present invention has been described in great detail with respect to preferred forms, many changes and variations are possible and will be apparent to those skilled in

What is claimed is:

1. An alkyltin compound of Formula 1:

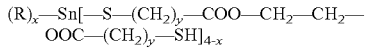
OOC—(CH$_2$)$_y$—SH]$_{4-x}$ wherein:
R is a methyl group;
x is 2;
y is 2; and
wherein the alkyltin compound of Formula 1 when added to a halogen-containing resin is effective to provide improved color stabilization in both initial color hold and long term heat stability relative to a halogen-containing resin having an added alkyltin compound derived from glycols with a divalent hydrocarbon radical containing more than two carbon atoms or relative to a halogen-containing resin having an added alkyltin compound without terminal thiol groups.

2. The compound of claim 1, wherein said compound is selected from the group consisting of dimethyltin bis(1,2-ethane dithioglycolate), monomethyltin tris(1,2-ethanedithioglycolate), dimethyltin bis(1,2-ethane dimercaptopropionate), monomethyltin tris(1,2-ethanedimercaptopropionate) and mixtures thereof.

3. A composition comprising a halogen-containing resin and an alkyltin compound of claim 1 in an amount effective to stabilize the resin against elevated temperatures.

4. The composition of claim 3, wherein said halogen-containing resin is a member of the group consisting of polyvinyl chloride, polyvinyl bromide, polyvinylidene chloride, copolymers of vinyl chloride and vinyl acetate, copolymers of vinyl chloride and vinylidene chloride, copolymers of vinyl chloride and acrylonitrile, copolymers of vinyl chloride and maleic or fumaric esters and copolymers of vinyl chloride and styrene.

5. The composition of claim 3, wherein said effective amount is within a range of from 0.5 to 1.80 parts stabilizer per hundred parts resin.

6. The composition of claim 5, wherein said range is from 0.8 to 1.2 parts stabilizer per hundred parts resin.

7. The composition of claim 4, further comprising at least one additive selected from the group consisting of lubricants, fillers, pigments, flame retardants, UV absorbers, impact modifiers and processing aids.

8. The composition of claim 7, wherein said lubricants are selected from the group consisting of calcium stearate, montan wax, fatty acid esters, polyethylene waxes, chlorinated hydrocarbons, glycerol esters and combinations thereof.

9. The composition of claim 8, wherein said fillers are selected from the group consisting of titanium oxide, calcium carbonate, kaolin, glass beads, glass fibers, talc, wood flour and mixtures thereof.

10. The composition of claim 7, wherein said pigments are selected from the group consisting of azo pigments, phthalocyanine pigments, quinacridone pigments, perylene pigments, diketopyrrolopyrrole pigments and anthraquinone pigments.

11. The composition of claim 7, wherein said flame retardants are selected from the group consisting of antimony oxide, molybdates, borates and hydroxystannates.

12. A method for preparation of the alkyltin compound of claim 1, comprising
I) esterifying ethylene glycol with a thioacid in a molar ratio of 1:2 in the presence of a suitable catalyst to produce a dithiol ester; and
II) reacting said dithiol ester with a tin-containing reactant at the following molar ratios: for dialkyltin derivatives S:Sn>1.5 and for monoalkyltin derivatives S:Sn>1.0.

13. The method of claim 12, wherein said tin-containing reactant is an alkyltin chloride or alkyltin oxide.

14. A method of stabilizing initial color of PVC consisting of adding to the PVC 1.12 phr of dimethyltin bis(1,2-ethane dithioglycolate), wherein the PVC has a yellow index of 3.59 at 3 minutes.

15. The method of claim 14, wherein the PVC has a yellow index of 5.99 at 6 minutes, and 7.93 at 9 minutes.

* * * * *